United States Patent [19]
Ohno

[11] Patent Number: 5,085,081
[45] Date of Patent: Feb. 4, 1992

[54] ULTRASONIC IMAGING APPARATUS WITHOUT PHASE DISTORTION

[75] Inventor: Masahiro Ohno, Kunitachi, Japan

[73] Assignee: Olympus Optical Co., Ltd., Tokyo, Japan

[21] Appl. No.: 617,386

[22] Filed: Nov. 15, 1990

Related U.S. Application Data

[63] Continuation of Ser. No. 325,675, Mar. 16, 1989, abandoned.

[30] Foreign Application Priority Data

Mar. 26, 1988 [JP] Japan .................... 63-72600

[51] Int. Cl.⁵ .......................... G01N 29/04
[52] U.S. Cl. ......................... 73/620; 73/642; 73/606; 73/629
[58] Field of Search ............... 73/602, 626, 618, 614, 73/620, 642, 606, 629

[56] References Cited

U.S. PATENT DOCUMENTS 4,077,253  3/1978  Grisell ..................... 73/606
4,804,249  2/1989  Reynolds et al. ........... 350/437
4,835,689  5/1989  O'Donnell ................. 73/626

FOREIGN PATENT DOCUMENTS 2520204  11/1976  Fed. Rep. of Germany .

OTHER PUBLICATIONS

"Generation and Detection of High-Order Harmonics in Liquids Using A Scanning Acoustic Microscope"; L. Germain and J. D. N. Cheeke; Journal of the Acoustic Society; pp. 942-949.

Primary Examiner—Hezron E. Williams
Assistant Examiner—Rose M. Finley
Attorney, Agent, or Firm—Frishauf, Holtz, Goodman & Woodward

[57] ABSTRACT

A high-frequency signal is applied from an oscillator via a circulator to a piezoelectric transducer. An ultrasonic wave generated by the piezoelectric transducer is directed to a material through an acoustic lens. The ultrasonic wave transmitted through the material is conducted to a phase-conjugator having a nonlinear piezoelectric element consisting of a crystal of LiNbO₃. A phase-conjugate wave generated by the generating section is transmitted through the material again and received by the piezoelectric transducer. The received signal is supplied to a receiver circuit via the circulator. The receiver circuit gates the received signal in accordance with a time of return of the phase-conjugate wave so as to extract a signal representing the interior of the material. The material is scanned two-dimensionally by a scanning control device so as to display a two-dimensional ultrasonic image on a television monitor.

28 Claims, 6 Drawing Sheets

ULTRASONIC IMAGING APPARATUS WITHOUT PHASE DISTORTION

This application is a continuation of application Ser. No. 07/325,675, filed Mar. 16, 1989 now abandoned.

BACKGROUND OF THE INVENTION

1. Field of the Invention

The present invention relates to an ultrasonic imaging apparatus for forming an image representing ultrasonic characteristics of a material by scanning the material with an ultrasonic wave.

2. Description of the Related Art

As conventional examples of such an apparatus, there are ultrasonic microscopes and ultrasonic probes, which are arranged to detect a reflected ultrasonic wave from or a transmitted ultrasonic wave through a material scanned with an ultrasonic wave and to form an ultrasonic image on the basis of the detected signal. In general, the apparatuses are exclusively used to know the internal acoustic (ultrasonic) characteristics of an opaque body, and the detected signals are displayed as a two-dimensional image representing the internal acoustic characteristics of the body.

In such imaging apparatuses, however, whether the reflected wave or the transmitted wave is utilized, the reflected wave from the interior of a material or the transmitted wave through the interior of the material is subject to phase distortion due to acoustic ununiformity of regions through which the ultrasonic wave travel. Therefore, simply detecting the reflected wave or transmitted wave by means of an ultrasound receiver in an attempt to form an ultrasonic image of the material may cause incident positions in the receiver on which ultrasonic waves fall to be varied due to a phase distortion. Therefore, the wavefront shape of the radiating wave and that of the incident wave become different at the transducer plane. This will adversely affect the obtained images. The effect of such phase distortion on the image is such that the contrast resulting from variations of direction of refraction of ultrasonic waves at a surface of the material, particularly at an uneven surface thereof, and the contrast produced by signals from the interior of the material appear simultaneously on an ultrasonic image in a mixed manner. It thus becomes difficult to understand the internal state of the material accurately. Moreover, where the surface state and the internal state of the material are compared, the accurate comparison becomes difficult.

SUMMARY OF THE INVENTION

It is a first object of the present invention to provide an ultrasonic imaging apparatus which compensates for the effect of phase distortion due to acoustic ununiformity of regions of a material through which ultrasonic waves travel and minimizes the effect of phase distortion in ultrasonic imaging.

It is a second object of the present invention to provide an ultrasonic imaging apparatus which permits an easy and accurate comparison between the surface state invention is arranged to generate a phase-conjugate wave of an ultrasonic wave transmitted through or reflected from the interior of a material, irradiates the material with the phase-conjugate wave again, and detect the phase-conjugate wave transmitted through or reflected from the material to form an ultrasonic image.

To attain the second object of the invention, the apparatus of the invention is arranged to form first and second ultrasonic images. More specifically, the apparatus detects an ultrasonic wave transmitted through or reflected from the interior of a material, separates at least a signal containing information indicative of a surface of the material from the detected signal and forms the first ultrasonic image on the basis of the separated signal. Moreover the apparatus generates a phase-conjugate wave of the ultrasonic wave transmitted through or reflected from the interior of the material, irradiates the material with the phase-conjugate wave again, detects the phase-conjugate wave transmitted through or reflected from the interior of the material and forms the second ultrasonic image on the basis of the detected signal.

DETAILED DESCRIPTION OF THE PREFERRED EMBODIMENTS

Figure 1:
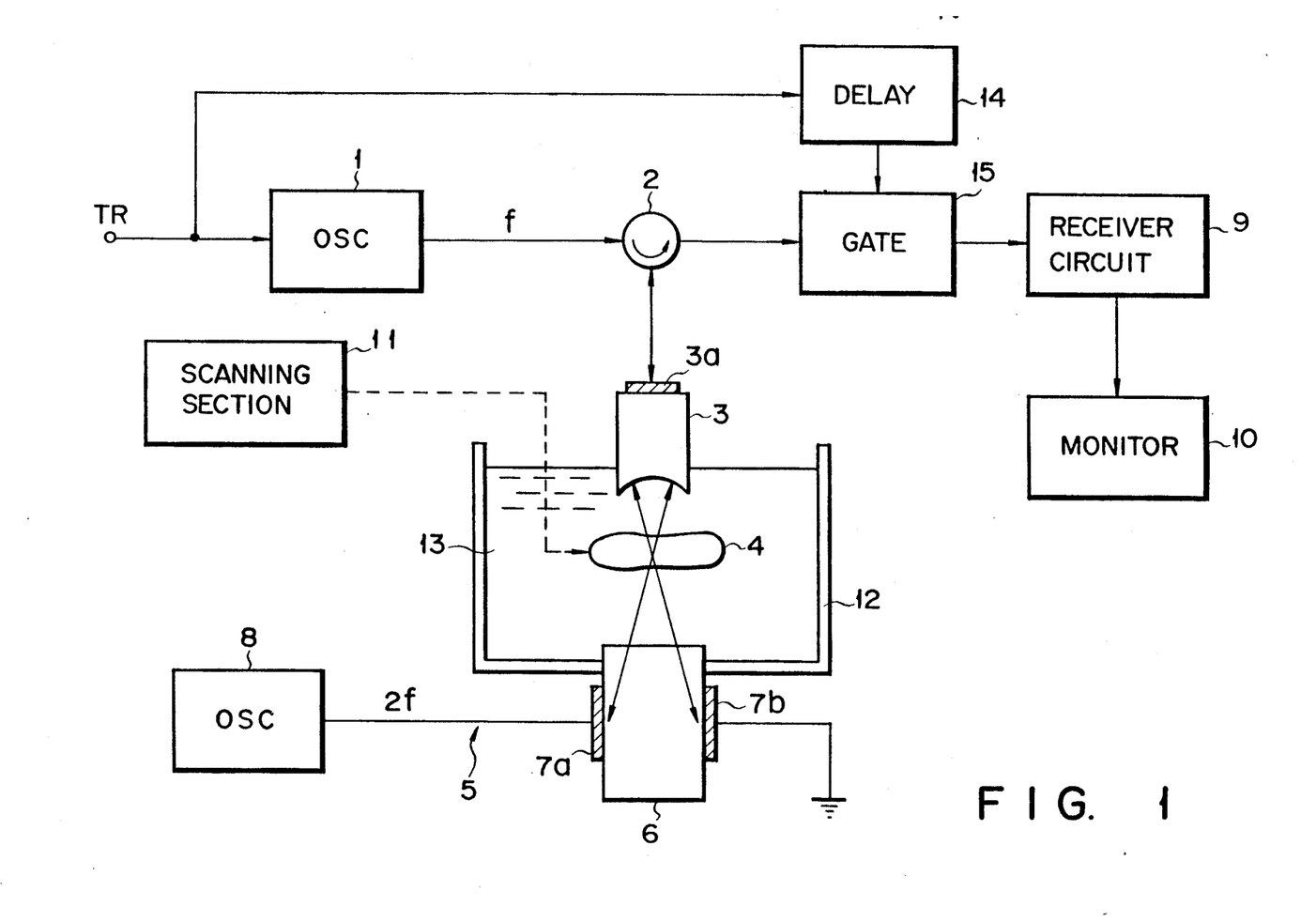
FIG. 1 is a schematic depiction of an ultrasonic imaging apparatus according to a first embodiment of the present invention.

In FIG. 1, there is illustrated an arrangement of an ultrasonic microscope which is a first embodiment of the present invention. A high-frequency signal whose frequency is f is fed from an oscillator 1 to a piezoelectric transducer 3a via a circulator 2. Piezoelectric transducer 3a is adhered to an acoustic lens 3. An ultrasonic wave generated by piezoelectric transducer 3a is directed to a material 4 via acoustic lens 3 and focused on a point of the material, i.e., the focus of acoustic lens 3. After the passage of the focus, the ultrasonic wave is transmitted through the material 4 while diverging from the focus. The ultrasonic wave which has been transmitted through the material 4 falls on a phase-conjugator which is generally indicated at 5.

Phase-conjugator 5 generates a wave which has reversed its travelling direction while keeping the shape of wavefront of the incident wave, i.e., a phase-conjugate wave. The phase-conjugator comprises of a nonlinear piezoelectric element 6 consisting of a crystal having acoustic nonlinearity, for example, $LiNbO_3$, electrodes 7a and 7b attached to nonlinear piezoelectric element 6 and an oscillator 8 for applying high-frequency voltage across nonlinear element 6 via electrodes 7a and 7b. In the nonlinear piezoelectric element 6, so called three-wave mixing is done by the incident ultrasonic wave, phase-conjugate wave, and electromagnetic wave. In this example, the frequency (=2f) of the high-frequency voltage from oscillator 8 is twice that of oscillator 1.

The phase-conjugate wave from nonlinear piezoelectric element 6 is transmitted through material 4 and received by piezoelectric transducer 3a for conversion to an electrical signal which is in turn applied to circulator 2a. An output signal of circulator 2 is applied to a receiver circuit 9 via a gate circuit 15 whose control terminal is supplied with a trigger signal TR, which is also applied to oscillator 1, via a delay circuit 14.

Figure 2:
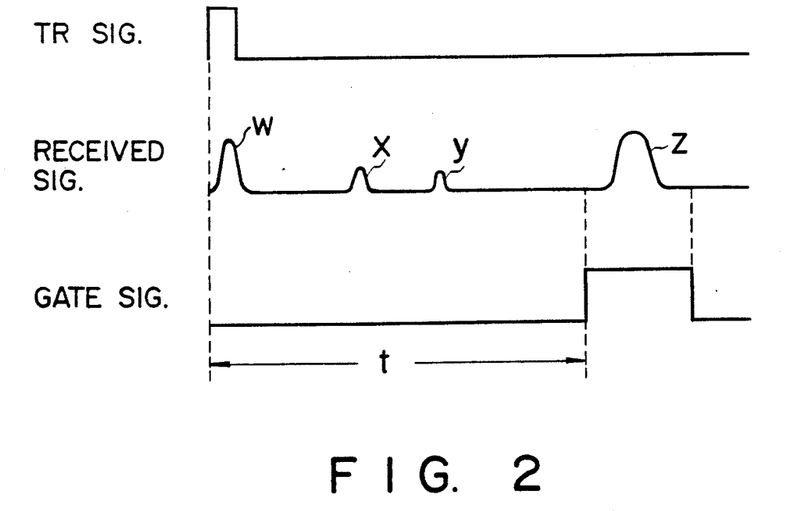
FIG. 2 is a timing diagram which is useful in understanding the operation of the first embodiment.

As shown in FIG. 2, after oscillator 1 starts oscillating, the receiver circuit 9 sequentially receives a leakage signal component w from circulator 2 of signals which are to be applied from oscillator 1 to piezoelectric element 3a, a signal component x based on an ultrasonic wave reflected from the transmission/receiving surface of piezoelectric element 3a, which are generated by piezoelectric element 3a to be directed to material 4, a signal component y based on an ultrasonic wave reflected from the surface of the material 4, which are generated by piezoelectric element 3a to transmit through the material, and a signal component z based on the phase-conjugate wave. Gate circuit 15 is thus provided to feed only the signal component z corresponding to the phase-conjugate wave into receiver circuit 9, which supplies a TV monitor 10 with the signal component z as a brightness signal. To this end, the gate circuit 15 is enabled by a control signal from delay circuit 14 after a delay of a predetermined time t corresponding to the distance between piezoelectric transducer 3a and nonlinear piezoelectric element 6 from a time of application of an oscillation triggering signal TR to oscillator 1.

The above operation is performed many times while scanning material 4 two-dimensionally by use of a scanning control section 11, so that a two-dimensional ultrasonic image can be displayed on TV monitor 10.

To avoid the attenuation of the ultrasonic wave propagating between acoustic lens 3 and nonlinear piezoelectric element 6 via material 4, a water tank 12 filled with an ultrasonic-wave transmission medium 13, such as water, is disposed between acoustic lens 3 and nonlinear acoustic element 6. Material 4 is immersed in medium 13 and the transmission/receiving surface of acoustic lens 3 and the input and output surface of nonlinear piezoelectric element 6 are in contact with medium 13.

The principle of compensation for the phase distortion according the present embodiment will now be described. A complex function representing a wave is generally expressed by $$f(r,t) = \text{Re}\{u(r)e^{j\omega t}\} \tag{1}$$

The phase-conjugate wave of this wave is expressed by $$f_c(r,t) = \text{Re}\{u^*(r)e^{j\omega t}\} \tag{2}$$

Here since $$\text{Re}\{u^*(r)e^{j\omega t}\} = \text{Re}\{u(r)e^{-j\omega t}\} \tag{3}$$

the phase-conjugate wave of the wave of equation (2) is given by $$f_c(r,t) = f(r,-t) \tag{4}$$

| | |
|---|---|
| f(r,t): | a complex function of space r and time t. |
| u(r): | a function which represents the spatial variation (of the function f(r,t)) |
| ω: | angular frequency |
| fc(r,t): | phase-conjugate wave of the function f(r,t) |

This means that the phase-conjugate wave is a time-reversal wave of the former wave. In other words, the phase-conjugate wave is a wave which has reversed its direction of propagation while keeping the shape of its wavefront. Accordingly, if a wave which has been subjected to the phase distortion by material 4 is directed to phase-conjugator 5 and its phase-conjugate wave generated is transmitted through material 4, then oppositely the transmitted wave will have the phase distortion offset.

Hence, if piezoelectric transducer 3a receives the phase-conjugate wave transmitted through material 4 and receiver circuit 9 receives only a signal corresponding to the phase-conjugate wave, an ultrasonic image will be formed on TV monitor 10, which is clear of or decreased in the contrast due to the surface state of material owing to the phase-distortion compensating capability of the phase-conjugate wave and has the contrast based on the difference in absorption quantity in the material. Particularly when there are air layers, such as cracks or bubbles, inside the material, the internal state of the material can be imaged in high contrast because the air layers are zero in transmittivity of ultrasonic waves.

Figure 3:
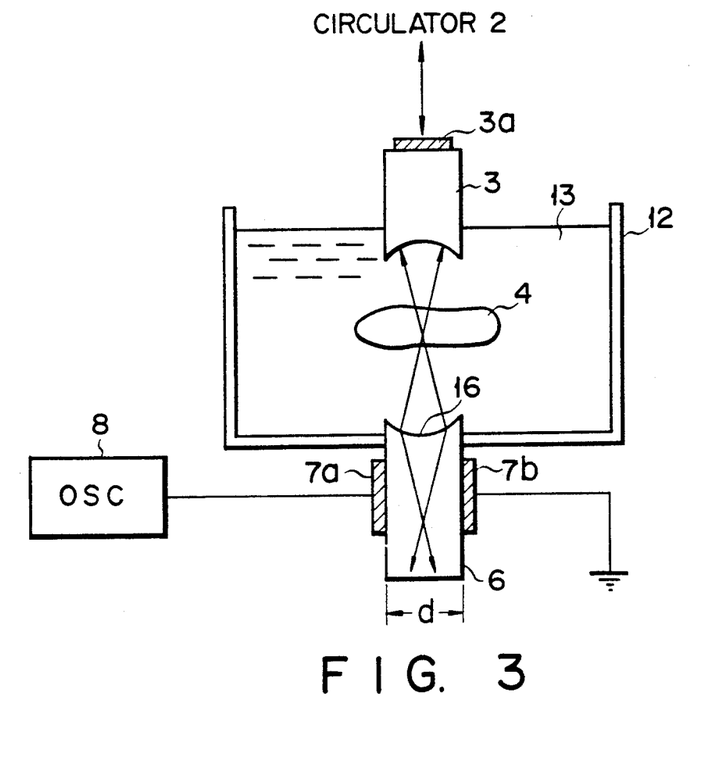
FIG. 3 is a schematic depiction of a second embodiment of the present invention.

FIG. 3 shows the principal part of a second embodiment of the present invention. In this embodiment, nonlinear piezoelectric element 6 of phase-conjugator 5 has its incident surface of transmitted ultrasonic waves from the material 4 shaped into a lens surface 16, not a mere plane as in the first embodiment. In other points the second embodiment is the same as the first embodiment.

By shaping the surface of nonlinear piezoelectric element 6 through which incoming and outgoing ultrasonic waves pass into lens form 16 as described above, the ultrasonic wave traveling through nonlinear piezoelectric element 6 can be concentrated into a narrow beam. That is, the beam intensity is increased as compared with the first embodiment. Thus the distance d between electrodes 7a and 7b can be made smaller than in the case of FIG. 1.

Intensity reflectance R of phase-conjugator 5 is defined as follows:

$$R = \tan^2(\alpha f E L / v^3) \tag{5}$$

where f is the frequency of ultrasonic wave, v is the speed of sound in nonlinear piezoelectric element 6, E is an amplitude of an applied electric field, L is the interaction length and α is a constant varying according to the type of nonlinear piezoelectric element 6. Usually since $$(\alpha f E L / v^3) << \pi \tag{6}$$

$$R \approx (\alpha f E L / v^3)^2 \tag{7}$$

Namely, the reflectance R becomes proportional to E If v is the applied voltage from oscillator 8 and d is the distance between electrodes 7a and 7b, then E is $$E = V/D \tag{8}$$

Hence the intensity reflectance R increases with decreasing distance d.

According to the second embodiment, therefore, since the distance d can be made small, the intensity reflectance R of nonlinear piezoelectric element 6 can be made great accordingly. It is thus possible to return a greater phase-conjugate wave to acoustic lens 3, which improves the carrier-to-noise ratio of an ultrasonic image.

Figure 4:
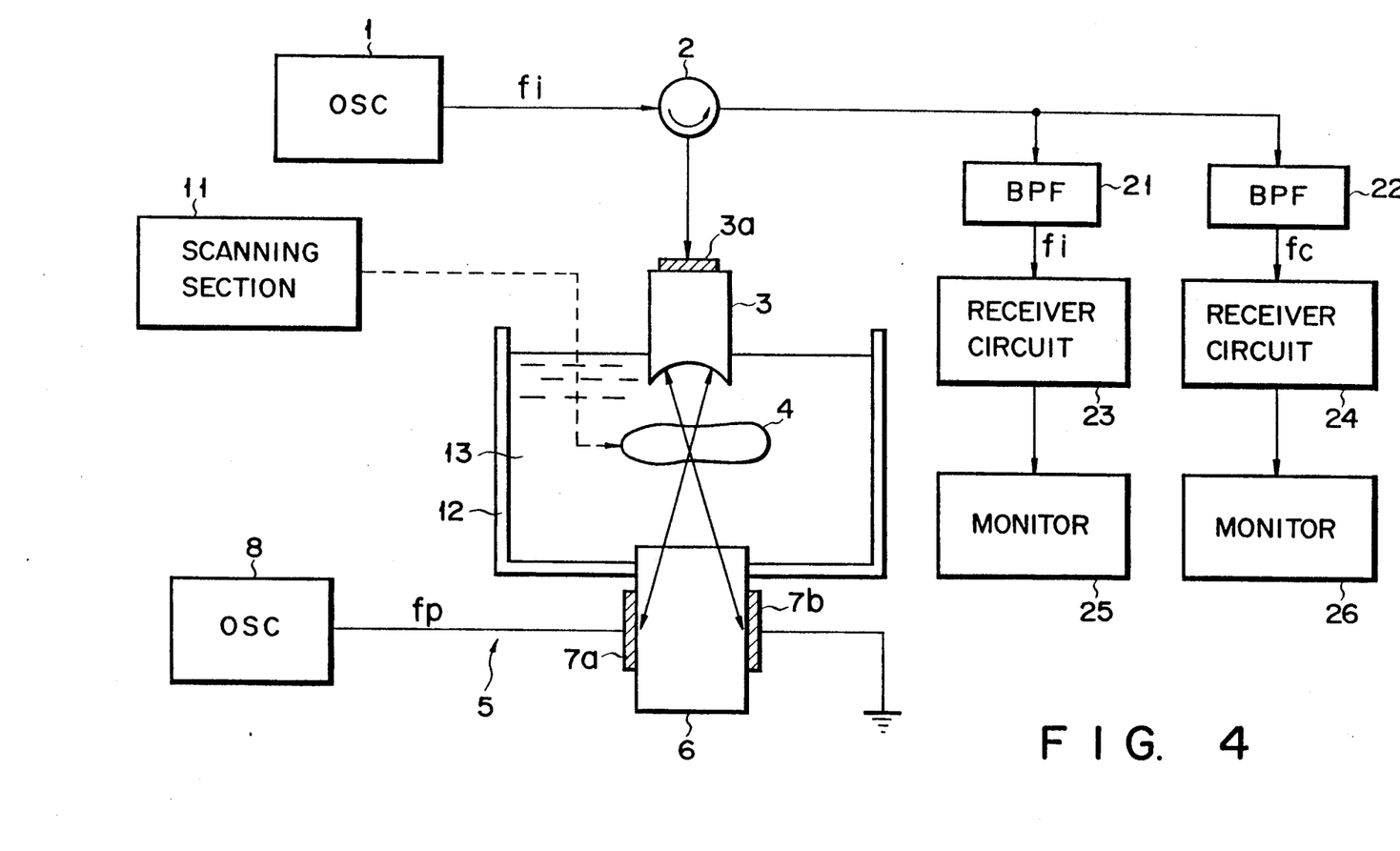
FIG. 4 is a schematic depiction of a third embodiment of the present invention.

FIG. 4 shows a third embodiment of the present invention. The third embodiment is different from the first embodiment in that oscillator 1 produces a high-frequency signal of a frequency of $f_i$, oscillator 8 produces a high-frequency signal of a frequency of $f_p$, signals received by piezoelectric transducer 3a are fed to receiver circuits 23 and 24 via bandpass filters 21 and 22 respectively centered at $f_i$ and $f_c$, the phase-conjugate wave frequency, and receiver circuits 23 and 24 respectively extract signals corresponding to the surface-reflected wave and the transmitted wave through material 4 for visual display on respective TV monitors 25 and 26. The frequencies $f_i$ and $f_p$ are set such that $$f_{1i} = (f_p/2) + \Delta f \quad (9)$$

and $$|\Delta f| << f_i \quad (10)$$

That is, fhd i is slightly deviated from the half of $f_p$.

With such an arrangement, the phase-conjugate wave of a transmitted wave through the material 4 is generated in nonlinear piezoelectric element 6 by means of three-wave mixing due to the nonlinear piezoelectric effect. The frequency $f_c$ of the phase-conjugate wave is $$f_c = f_p - f_i = (f_p/2) - \Delta f$$

Namely $f_c$ is deviated from $f_i$ by $2\Delta f$.

Figure 5:
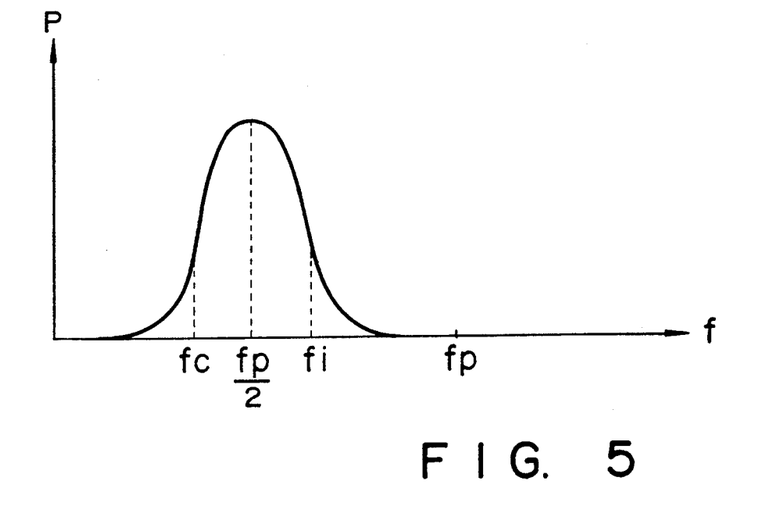
FIG. 5 shows the principle of the third embodiment.

FIG. 5 shows the characteristic of gain P of the phase-conjugate wave with respect to ultrasonic-wave frequency f. The phase-conjugate wave is generated when $f_i$ and $f_p$ are set such that $f_i$ is close to $f_p/2$ ($f_i = (f_p/2) + \Delta f$) and its gain becomes maximum at $f = f_p/2$.

Accordingly, by passing the received signal received by piezoelectric element 3a through bandpass filters 21 and 22 centered at $f_i$ and $f_c$, respectively, it becomes possible to frequency discriminate the phase-conjugate wave and the ultrasonic wave. Thus receiver circuit 23 picks up and supplies a signal of the surface-reflected wave from material 4 to TV monitor 5, by means of amplification and gating, for visually displaying an ultrasonic image representing the surface state of material 4, while receiver circuit 26 picks up and supplies a signal of the transmitted wave through material 4 to TV monitor 26, by means of amplification, for visually displaying an ultrasonic image representing the internal state of material 4. And moreover, the ultrasonic image representing the internal state of material 4 displayed on TV monitor 26 has the contrast due to the surface shape of material 4 removed or decreased owing to the phase-distortion compensating capability of the phase-conjugate wave. Therefore, by comparison between the images on TV monitors 25 and 26, it is possible to understand the acoustic properties of the surface and the interior of material 4 easily and accurately.

According to the third embodiment, since the frequencies of oscillators 1 and 8 are set as described above, the signal representing the internal state of material 4 can be extracted from all the received signals by frequency discrimination.

Figure 6:
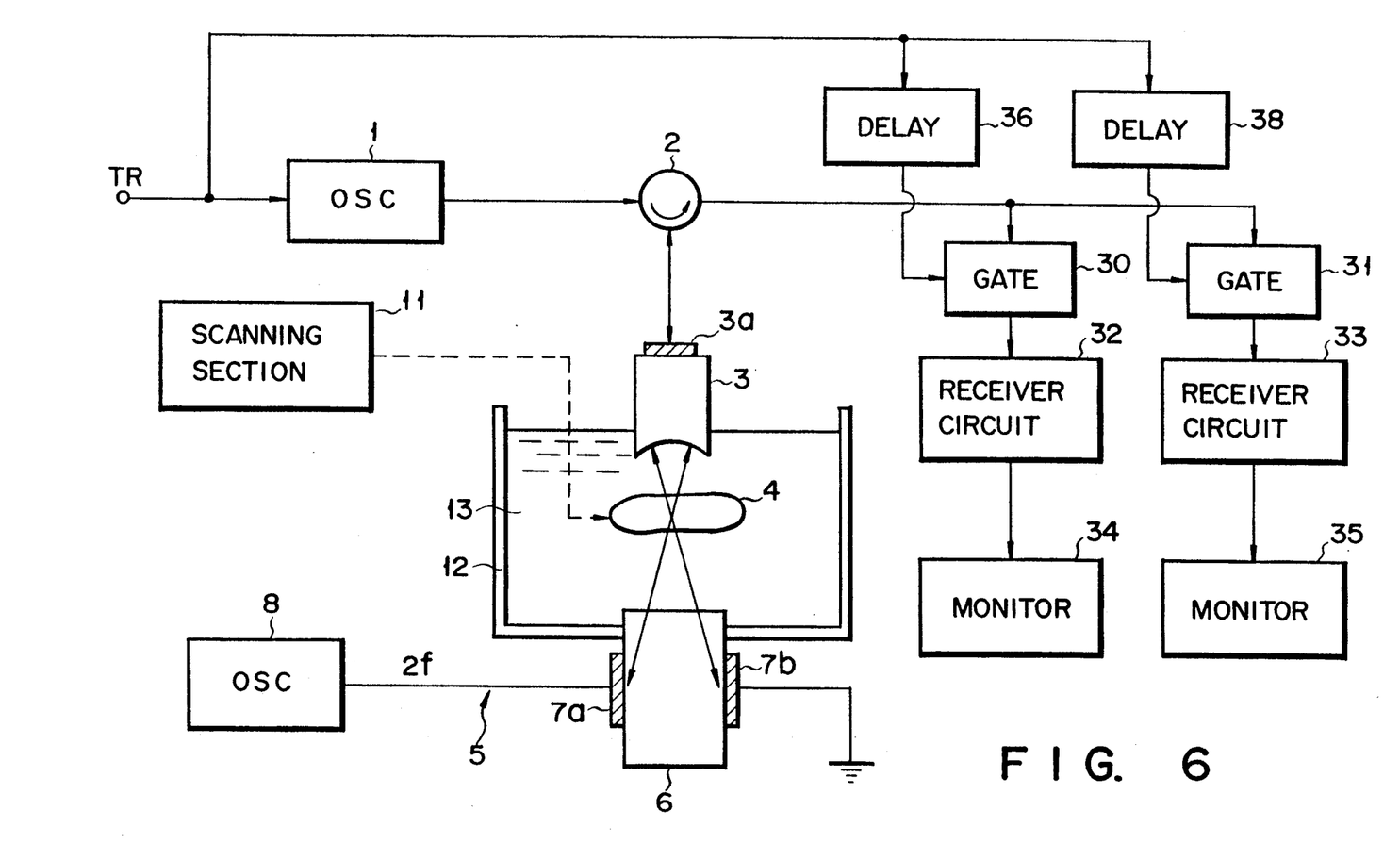
FIG. 6 is a schematic illustration of a fourth embodiment of the present invention.

Illustrated in FIG. 6 is a fourth embodiment of the present invention in which the signal received by piezoelectric element 3a is applied to receiver circuits 32 and 33 via gate circuits 30 and 31, respectively. Gate circuit 30 is adapted to extract a surface-reflected wave signal from material 4 which arrives earlier than a phase-conjugate wave, while gate circuit 31 is adapted to extract a signal corresponding to the phase-conjugate wave which arrives later than the surface-reflected signal. Gate circuits 30 and 31 are supplied with trigger signal TR for oscillator 1 via delay circuits 36 and 38, respectively. The delay time of delay circuit 38 is the same as that of delay circuit 14 in the first embodiment, while the delay time of delay circuit 36 is equal to the time interval between the trigger signal TR and the signal component y in FIG. 2. Thus, monitor 34 displays a surface image, while monitor 35 displays an internal image. The other portions are the same as those of FIG. 1.

In this embodiment, as in the first through third embodiments, the image displayed on TV monitor 35 has the contrast resulting from the surface shape of material 4 removed or decreased and represents the internal state of material 4 with the contrast based on the absorption difference within the material. Thus the comparison between images displayed on monitors 34 and 35 will permit the easy and accurate understanding of the acoustic properties of the surface and the interior of material 4.

Although the preferred embodiments of the present invention have been disclosed and described, it is apparent that other embodiments and modifications are possible. For example, the arrangement of FIG. 3 in which nonlinear piezoelectric element 6 has lens surface 16 may effectively be applied to the embodiments of FIGS. 4 and 6.

Figure 7:
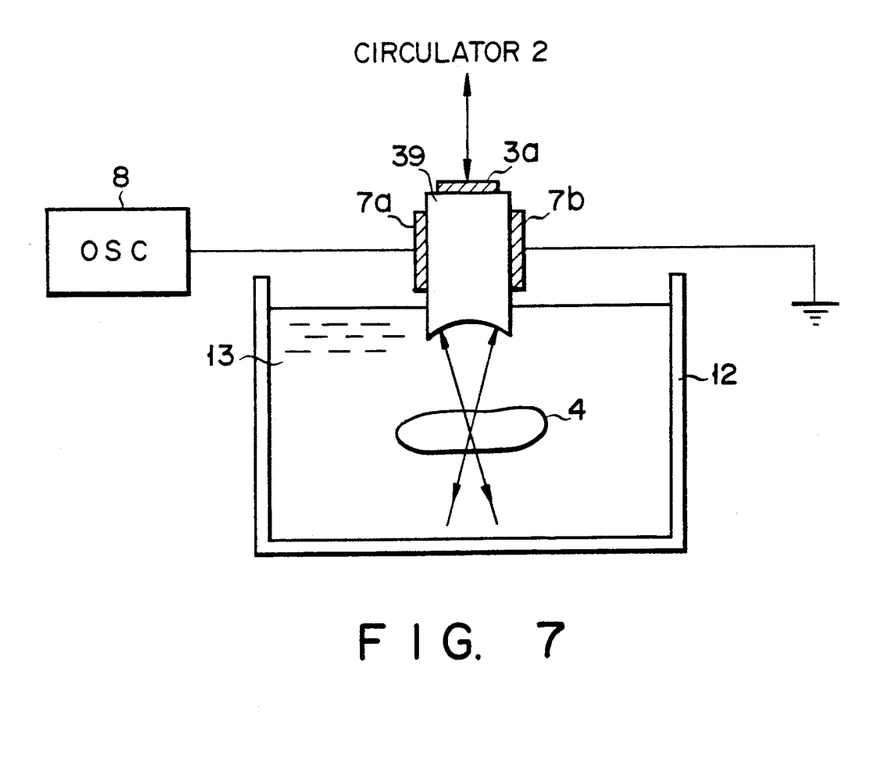
FIG. 7 shows a modified phase-conjugator which may be used in each of the embodiments.

Although the above embodiments are all of transmissive type, a reflective type may be made by interposing the nonlinear piezoelectric element generating the phase-conjugate wave between the material and the acoustic lens. In such a reflective type, the nonlinear piezoelectric element may be made integral with the acoustic lens 39 using the same material, e.g., $LiNbO_3$, as shown in FIG. 7.

Figure 8:
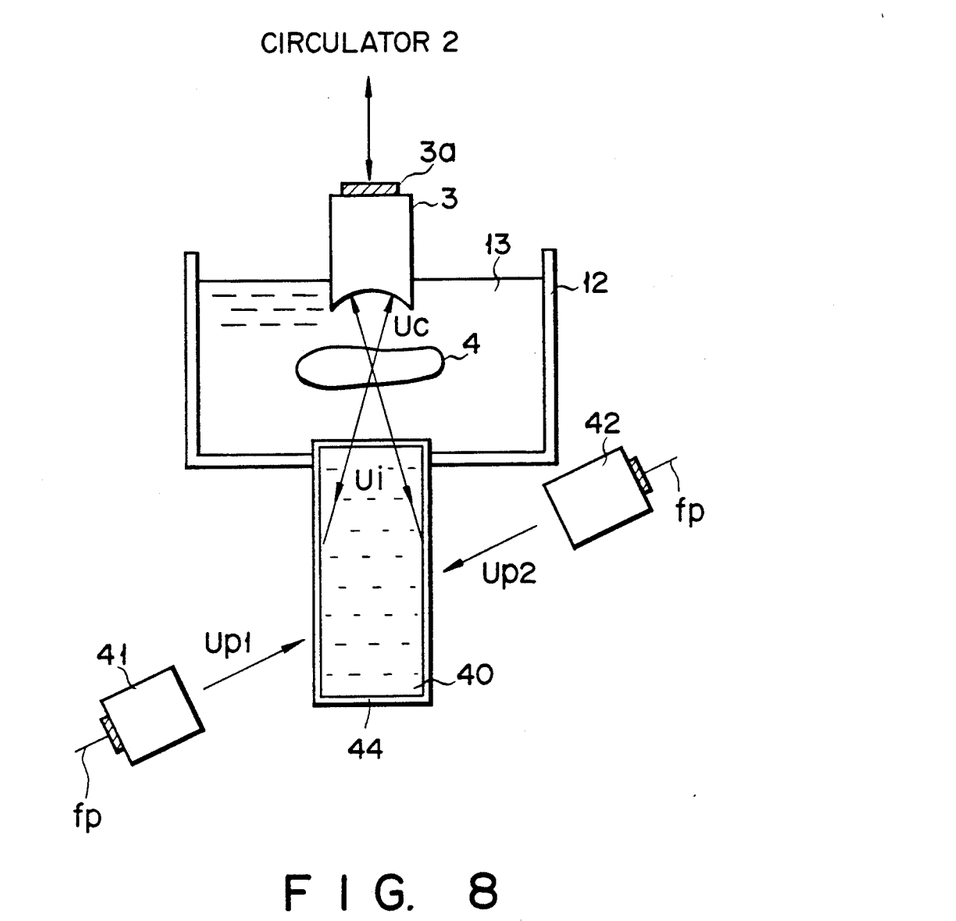
FIG. 8 shows a modified phase-conjugator which may be used in the third embodiment.

Furthermore, the phase-conjugator may be constructed by use of any other material than the nonlinear piezoelectric element. In the case of FIG. 4, for example, phase-conjugate wave generating means 5 may comprise a medium 40 having the third-order nonlinearity, such as water having air bubbles or micro particles, and a pair of ultrasound sources 41 and 42 opposed to each other with medium 40 interposed therebetween. The medium 40 is filled in a container 44. In the present case, ultrasonic wave Ui (frequency $f_i$) from piezoelectric transducer 3a and ultrasonic waves Up1 and Up2 (frequency $f_p$) from ultrasound sources 41 and 42 each of which is formed by a transducer and oscillator are directed to medium 40, thereby generating a phase-conjugate wave Uc by means of four-wave mixing. The frequency of phase-conjugate wave Uc becomes $f_c = 2f_p - f_i$. If $f_i = f_p + \Delta f$, then $f_c = f_p - \Delta f$. Obviously the frequency discrimination is possible.

The scanning of the material with an ultrasonic wave may be performed by moving both the acoustic lens and the phase-conjugator with the material fixed, instead of moving the material. Alternatively the material, acoustic lens and phase-conjugator may all be moved.

According to the present invention, as described above, since a phase-conjugate wave is generated and detected, an accurate ultrasonic image can be formed, which has the phase distortion resulting from the shape of the material removed and decreased. Moreover, since a usual ultrasonic image containing information of the surface of the material is formed in addition to the ultrasonic image based on the phase-conjugate wave, the comparison between two images permits the easy and accurate understanding of the acoustic properties of the surface and interior of the material. Accordingly, in the present invention, ceramics or metal parts whose surface is not even or living cells having internal acoustic nonuniformity, which are difficult to inspect and measure with conventional ultrasonic microscopes or flow detectors, can easily be observed with accuracy.

What is claimed is:

1. An apparatus for irradiating a material with an ultrasonic wave and detecting ultrasonic characteristics of the material, comprising:
    means for scanning the material with an ultrasonic wave, the ultrasonic wave being transmitted toward a limited portion of the material;
    phase-conjugate wave generating means for receiving said ultrasonic wave transmitted through or reflected from the material and generating and directing a phase-conjugate wave of the ultrasonic wave to the material; and
    means for detecting the phase-conjugate wave transmitted through or reflected from the material.

2. The apparatus according to claim 1, in which said phase-conjugate wave generating means comprises a nonlinear piezoelectric element on which the ultrasonic wave transmitted through or reflected from the material falls, and an oscillator for supplying a high-frequency voltage of a predetermined frequency to said nonlinear piezoelectric element.

3. The apparatus according to claim 2, in which the frequency of the high-frequency voltage is twice the frequency of the ultrasonic wave with which the material is irradiated.

4. The apparatus according to claim 3, in which said detecting means includes a gate for passing a received signal therethrough after a delay of time corresponding to a distance between said detecting means and said phase-conjugate wave generating means from the start of irradiation of the material with the ultrasonic wave.

5. The apparatus according to claim 2, in which the oscillation frequency of said oscillator is two times the frequency of the ultrasonic wave with which the material is irradiated minus the difference in frequency between the ultrasonic wave and the phase-conjugate wave.

6. The apparatus according to claim 5, in which said detecting means includes a bandpass filter centered at the oscillation frequency of said oscillator.

7. The apparatus according to claim 2, in which said nonlinear piezoelectric element consists of a crystal of $LiNbO_3$.

8. The apparatus according to claim 2, in which said nonlinear piezoelectric element has a lens surface on which the ultrasonic wave falls.

9. An ultrasonic imaging apparatus comprising:
    ultrasonic wave transmitting/receiving means for transmitting an ultrasonic wave to a material and receiving an ultrasonic wave;
    scanning means for scanning the material with said ultrasonic wave by two-dimensionally moving at least one of said transmitting/receiving means and the material;
    phase-conjugate wave generating means for receiving an ultrasonic wave transmitted through or reflected from the material and generating and transmitting a phase-conjugate wave of the ultrasonic wave; and
    image forming means for extracting an ultrasonic wave reflected from a surface of the material and the phase-conjugate wave generated by said phase-conjugate wave generating means and transmitted through or reflected from the material from the ultrasonic wave received by said transmitting/receiving means to form an image representing ultrasonic characteristics of the surface of the material and an image representing ultrasonic characteristics of the interior of the material.

10. The apparatus according to claim 9, in which said transmitting/receiving means includes a piezoelectric element, an acoustic lens contacting said piezoelectric element, a first oscillator for generating a high-frequency voltage of a first frequency, and a circulator for supplying the high-frequency voltage from said first oscillator to said piezoelectric element and supplying an electrical signal corresponding to a received wave output from said piezoelectric element to said image forming means.

11. The apparatus according to claim 10, in which said phase-conjugate wave generating means includes a nonlinear piezoelectric element on which an ultrasonic wave transmitted through or reflected from the material falls, and a second oscillator for supplying a high-frequency voltage of second frequency to said nonlinear piezoelectric element.

12. The apparatus according to claim 11, in which the oscillation frequency of said second oscillator is twice that of said first oscillator.

13. The apparatus according to claim 12, in which said image forming means includes a first gate for passing a received signal after a delay of time corresponding to a distance between said piezoelectric element and the material from the start of transmission of the ultrasonic waves to the material, and a second gate for passing a received signal after a delay of time corresponding to a distance between said piezoelectric element and said phase-conjugate wave generating means from the start of transmission of the ultrasonic waves to the material.

14. The apparatus according to claim 11, in which the oscillation frequency of said second oscillator is two times the oscillation frequency of said first oscillator minus the difference between the oscillation frequency of said first oscillator and the frequency of the phase-conjugate wave.

15. The apparatus according to claim 14, in which said image forming means includes a first bandpass filter centered at the oscillation frequency of said first oscillator, and a second bandpass filter centered at the frequency of the phase-conjugate wave.

16. The apparatus according to claim 11, in which said nonlinear piezoelectric element consists of a crystal of $LiNbO_3$.

17. The apparatus according to claim 11, in which said nonlinear piezoelectric element has a lens surface on which the ultrasonic wave falls.

18. The apparatus according to claim 9, in which said transmitting/receiving means includes a piezoelectric element, an acoustic lens contacting said piezoelectric element, a first oscillator for supplying a high-frequency voltage of a first frequency to said piezoelectric element, and said phase-conjugate wave generating means includes a second oscillator for supplying a high-frequency voltage of a second frequency to said acoustic lens.

19. The apparatus according to claim 9, in which the material is placed in a container containing an ultrasonic-wave transmitting medium, and an ultrasonic transmitting/receiving surface of each of said transmitting- /receiving means and said phase-conjugate wave generating means contacts said medium in said container.

20. An ultrasonic apparatus for transmitting an ultrasonic wave to a material to detect an ultrasonic property of the material, comprising:
  ultrasonic wave transmitting means for transmitting an ultrasonic wave to a material;
  phase-conjugate wave generating means for receiving said ultrasonic wave transmitted through the material and generating and directing a phase-conjugate wave of the ultrasonic wave to the material; and
  ultrasonic wave receiving means for receiving a phase-conjugate wave generated from said phase-conjugate wave generating means and transmitted through the material, the ultrasonic wave receiving means receiving the phase-conjugate wave at the same location as the ultrasonic wave transmitting means.

21. The apparatus according to claim 20, in which said phase-conjugate wave generating means comprises a nonlinear piezoelectric element on which the ultrasonic wave transmitted through the material falls, and an oscillator for supplying a high-frequency voltage of a predetermined frequency to said nonlinear piezoelectric element.

22. The apparatus according ot claim 21, in which the frequency of the high-frequency voltage is twice the frequency of the ultrasonic wave which is transmitted to the material.

23. The apparatus according to claim 22, further comprising detecting means for detecting the phase-conjugate wave transmitted through the material, and wherein said detecting means includes a gate for passing a received signal therethrough after a delay of time corresponding to a distance between said detecting means and said phase-conjugate wave generating means from the start of transmission of the ultrasonic wave to the material.

24. The apparatus according to claim 21, in which the oscillation frequency of said oscillator is two times the frequency of the ultrasonic wave with which the material is irradiated minus the difference in frequency between the ultrasonic wave and the phase-conjugate wave.

25. The apparatus according to claim 24, further comprising detecting means for detecting the phase-conjugate wave transmitted through the material, and wherein said detecting means includes a band-pass filter centered at the oscillation frequency of said oscillator.

26. The apparatus according to claim 21, in which said nonlinear piezoelectric element consists of a crystal of $LiNbO_3$.

27. The apparatus according to claim 21, in which said nonlinear piezoelectric element has a lens surface on which the ultrasonic wave falls.

28. The apparatus according to claim 20, wherein said ultrasonic wave receiving means and said ultrasonic wave transmitting means are in the form of a single transducer.

* * * * *